United States Patent
Younis et al.

(10) Patent No.: US 12,115,202 B1
(45) Date of Patent: Oct. 15, 2024

(54) **METHOD OF PREVENTING CADMIUM-INDUCED LIVER TOXICITY USING A PLANT PRODUCT DERIVED FROM *ACHILLEA MILLEFOLIUM* L**

(71) Applicant: KING FAISAL UNIVERSITY, Al Hasa (SA)

(72) Inventors: Nancy S Younis, Al Hasa (SA); Maged E S Mohamed, Al Hasa (SA)

(73) Assignee: KING FAISAL UNIVERSITY, Al Hasa (SA)

( * ) Notice: Subject to any disclaimer, the term of this patent is extended or adjusted under 35 U.S.C. 154(b) by 0 days.

(21) Appl. No.: 18/407,411

(22) Filed: Jan. 8, 2024

(51) Int. Cl.
*A61K 36/28* (2006.01)
*A61P 1/16* (2006.01)

(52) U.S. Cl.
CPC .............. *A61K 36/28* (2013.01); *A61P 1/16* (2018.01); *A61K 2236/31* (2013.01)

(58) Field of Classification Search
CPC ..................................................... A61K 36/28
See application file for complete search history.

(56) References Cited

FOREIGN PATENT DOCUMENTS

| | | |
|---|---|---|
| IN | 201911008041 | 9/2020 |
| IN | 202341055041 | 9/2023 |
| RU | 2467742 C1 * | 11/2012 |

OTHER PUBLICATIONS

Jeyaprakash, K., and P. Chinnaswamy. "Effect of Spirulina and Liv-52 on cadmium induced toxicity in albino rats.", Indian J. Exp. Biol., Sep. 2005.

Rathore, Premlata, et al. "Hepatoprotective activity of isolated herbal compounds" Research Journal of Pharmacy and Technology 7.2 (2014): 229-234.

Seeff, Leonard B., et al. "Complementary and alternative medicine in chronic liver disease." Hepatology 34.3 (2001): 595-603.

Alzomor, Abdulkarim KY, and H. Nada. "Al-Absi, Abubaker F. Al-hssany, Helmy S. Al-Salahi, Ashgan A. Almushra'a (2022). Investigate the Effects of Achillea millefolium Plant Extract as A Hepatoprotection on Carbon Tetrachloride-Induced Liver Toxicity in Female Rats." Saudi J Med Pharm Sci 8.5: 227-233.

Cimen O, Eken H, Keskin Cimen F, Cekic AB, Kurt N, Ozbek Bilgin A, Suleyman B, Suleyman H, Mammadov R, Pehlivanoglu K, Kurnaz E. "The effect of Liv-52 on liver ischemia reperfusion damage in rats", BMC Pharmacol Toxicol. Jan. 3, 2020;21(1).

* cited by examiner

*Primary Examiner* — Qiuwen Mi (74) *Attorney, Agent, or Firm* — Nath, Goldberg & Meyer; Joshua B. Goldberg

(57) ABSTRACT

A method of preventing cadmium-induced liver toxicity can include administering an a plant product derived from *Achillea millefolium* L. to a subject in need thereof. In an embodiment, the plant product is selected from an essential oil of *Achillea millefolium* L.

19 Claims, 4 Drawing Sheets
Specification includes a Sequence Listing.

METHOD OF PREVENTING CADMIUM-INDUCED LIVER TOXICITY USING A PLANT PRODUCT DERIVED FROM *ACHILLEA MILLEFOLIUM* L

SEQUENCE LISTING

The instant application contains a Sequence Listing which has been submitted in XML format via Patent Center and is hereby incorporated by reference in its entirety. Said XML copy, created on Dec. 12, 2023, is named YOUNIS_et_al_sequence.xml and is 9,482 bytes in size.

BACKGROUND

1. Field

The disclosure of the present patent application relates to preventing cadmium toxicity, and particularly, to preventing cadmium toxicity using a plant product derived from *Achillea millefolium* L.

2. Description of the Related Art

*Achillea millefolium* L., commonly known as yarrow, is a flowering plant of the *Achillea* Asteraceae family. The plant is native to Asia, Europe, and North America. Several species have been employed as garden ornaments. Due to its antiphlogistic, spasmolytic, stomachic, carminative, and cholagogue properties, the plant has been used for medicinal purposes. While yarrow is most used in the treatment of gastrointestinal disorders, it is also utilized as a bitter aromatic, to increase bile output, and as an antioxidant.

In general, cadmium is used to manufacture nickel-cadmium rechargeable batteries, metal plating, and rods in nuclear reactors to control atomic fission reaction. Cadmium is a soft, malleable, ductile, and bluish white metal with respective atomic number, atomic mass, and electronic configuration viz. 48, 112.4, and [Kr] $4d^{10}5s^2$. It is considered a highly toxic non-essential heavy metal and is a suspected carcinogen. Cadmium contamination typically occurs from occupational exposure, consumption of contaminated food or water, and cigarette smoking. Acute toxicity can severely damage the liver, renal and reproductive systems, and red blood corpuscles.

Thus, a method of preventing cadmium-induced liver toxicity solving the aforementioned problems are desired.

SUMMARY

The present subject matter relates to a method of preventing cadmium-induced liver toxicity, comprising administering a plant product derived from *Achillea millefolium* L. to a patient in need thereof. In an embodiment, the plant product is selected from an essential oil of *Achillea millefolium* L. In an embodiment, a method of preventing cadmium-induced liver toxicity can include administering the essential oil of *Achillea millefolium* L to a patient in need thereof.

In other embodiments, the present subject matter relates to a method of preventing cadmium-induced liver toxicity comprising administering a pharmaceutical composition comprising a plant product derived from *Achillea millefolium* L. and a pharmaceutically acceptable carrier.

These and other features of the present subject matter will become readily apparent upon further review of the following specification and drawings.

DETAILED DESCRIPTION OF THE PREFERRED EMBODIMENTS

The following definitions are provided for the purpose of understanding the present subject matter and for construing the appended patent claims.

Definitions

It should be understood that the drawings described above or below are for illustration purposes only. The drawings are not necessarily to scale, with emphasis generally being placed upon illustrating the principles of the present teachings. The drawings are not intended to limit the scope of the present teachings in any way.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

A "subject" herein is typically a human. In certain embodiments, a subject is a non-human mammal. Exemplary non-human mammals include laboratory, domestic, pet, sport, and stock animals, e.g., mice, cats, dogs, horses, and cows. Typically, the subject is eligible for treatment, e.g., treatment of a gastrointestinal inflammatory disorder such as ulcerative colitis.

As used herein, the term "patient" refers to any single subject for which treatment is desired. In certain embodiments, the patient herein is a human. A subject can be considered to be in need of treatment.

An "effective amount" of a composition as described herein is an amount sufficient to carry out a specifically stated purpose. An "effective amount" may be determined empirically and in a routine manner, in relation to the stated purpose. The term "therapeutically effective amount" refers to an amount of a composition as described herein to "treat" a disease or disorder in a subject.

"Reducing", "reduce", or "reduction" means decreasing the severity, frequency, or length of one or more symptoms of a disease, disorder, or condition as described herein.

"Treating" or "treatment" or "alleviation" refers to both therapeutic treatment and prophylactic or preventative measures, wherein the object is to prevent or slow down (lessen) the targeted pathologic disease, condition, or disorder. Those in need of treatment include those already with the disease, condition, or disorder as well as those prone to have the disease, condition, or disorder or those in whom the disease, condition, or disorder is to be prevented. A subject or mammal is successfully "treated" for a disease, condition, or disorder if, after receiving a therapeutic amount of a composition as described herein, the subject shows observable and/or measurable reduction in, or absence of, one or more symptoms of the disease, condition, or disorder. Reduction of these signs or symptoms may also be felt by the patient.

The present subject matter relates to a method of preventing cadmium-induced liver toxicity, comprising administering a plant product derived from *Achillea millefolium* L. to a subject in need thereof. In an embodiment, the plant product is selected from an essential oil of *Achillea millefolium* L. (also identified herein as *Achillea* Essential Oil (AEO))

In one aspect, the present subject matter relates to a method of preventing cadmium-induced liver toxicity comprising administering an essential oil of *Achillea millefolium* L. to a subject in need thereof. In an embodiment, the sample is obtained from at least one of the stem, leaf, and flower of *Achillea millefolium* L.

In one aspect, the present subject matter relates to a method of preventing cadmium-induced liver toxicity comprising administering an essential oil of *Achillea millefolium* L. to a subject in need thereof. In an embodiment, the essential oil of *Achillea millefolium* L. is prepared by drying the aerial parts of *Achillea millefolium* L. to provide a dried sample; subjecting the dried sample to hydro-distillation to provide a volatile fraction; and drying the volatile fraction to provide the essential oil. In one embodiment, the volatile fraction is recovered by decantation and dried over anhydrous sodium sulphate to provide the essential oil.

In another aspect, the present subject matter relates to a method of preventing cadmium-induced liver toxicity, comprising administering an essential oil of *Achillea millefolium* L. to a subject in need thereof. In one embodiment, the essential oil of *Achillea millefolium* L. can be obtained from oils collected from at least one of the stem, leaf, and flowers of *Achillea millefolium* L.

An embodiment of the present subject matter is directed to a pharmaceutical composition comprising a plant product *Achillea millefolium* L. and a pharmaceutically acceptable carrier. In an embodiment, the plant product is selected from an essential oil of *Achillea millefolium* L.

An embodiment of the present subject matter is directed to a method of making a pharmaceutical composition including mixing the plant product of *Achillea millefolium* L. with a pharmaceutically acceptable carrier. For example, the method of making a pharmaceutical composition can include mixing the plant product of *Achillea millefolium* L. with a pharmaceutically acceptable carrier with preservatives, buffers, and/or propellants to create the pharmaceutical composition.

To prepare the pharmaceutical composition, the plant product of *Achillea millefolium* L., as the active ingredient, is intimately admixed with a pharmaceutically acceptable carrier according to conventional pharmaceutical compounding techniques. Carriers are inert pharmaceutical excipients, including, but not limited to, binders, suspending agents, lubricants, flavorings, sweeteners, preservatives, dyes, and coatings. In preparing compositions in oral dosage form, any of the pharmaceutical carriers known in the art may be employed. For example, for liquid oral preparations, suitable carriers and additives include water, glycols, oils, alcohols, flavoring agents, preservatives, coloring agents, and the like. Further, for solid oral preparations, suitable carriers and additives include starches, sugars, diluents, granulating agents, lubricants, binders, disintegrating agents, and the like.

The present compositions can be in unit dosage forms such as tablets, pills, capsules, powders, granules, ointments, sterile parenteral solutions or suspensions, metered aerosol or liquid sprays, drops, ampules, auto-injector devices or suppositories, for oral parenteral, intranasal, sublingual or rectal administration, or for administration by injection, inhalation or insufflation. The plant product of *Achillea millefolium* L. can be mixed under sterile conditions with a pharmaceutically acceptable carrier and, if required, any needed preservatives, buffers, or propellants. The composition can be presented in a form suitable for daily, weekly, or monthly administration. The pharmaceutical compositions herein will contain, per dosage unit, e.g., tablet, capsule, powder, injection, teaspoonful, suppository and the like, an amount of the active ingredient necessary to deliver an effective dose. A therapeutically effective amount of the plant product of *Achillea millefolium* L. or an amount effective to treat a disease, such as a cadmium-induced liver toxicity, may be determined initially from the Examples described herein and adjusted for specific targeted diseases using routine methods.

The pharmaceutical composition can be administered to a subject in need thereof, particularly in a therapeutically effective amount, which applies to all treatment methods described herein. In an embodiment, the pharmaceutical composition can be administered to a subject in need thereof to treat cadmium-induced liver toxicity.

The plant product of *Achillea millefolium* L. or pharmaceutical compositions thereof can be administered to a subject by any suitable route. For example, the compositions can be administered orally (including bucally and sublingually), nasally, rectally, intracisternally, intra vaginally, intraperitoneally, topically, transdermally (as by powders, ointments, or drops), and/or parenterally. As used herein, "parenteral" administration refers to modes of administration other than through the gastrointestinal tract, which include intravenous, intramuscular, intraperitoneal, intrasternal, intramammary, intraocular, retrobulbar, intrapulmonary, intrathecal, subcutaneous and intraarticular injection and infusion. Surgical implantation may also be contemplated, including, for example, embedding a composition of the disclosure in the body such as, for example, in a tissue, in the abdominal cavity, under the splenic capsule, brain, or in the cornea.

The present teachings are illustrated by the following examples.

Example 1

Preparing of Essential Oil of *Achillea millefolium* L.

The dried whole aerial parts of Yarrow (*Achillea millefolium* L.) were collected from local farms in Al-Ahsa, Eastern province, Kingdom of Saudi Arabia. The plant was identified by plant taxonomists in both Saudi Arabia and Egypt.

The *A. millefolium* aerial parts (100 g) were dried, cut, and subjected to hydro-distillation using Clevenger-type apparatus for 3 hours. The resulting volatile fraction (yield; 0.85% v/dried weight) was recovered by decantation and dried over anhydrous sodium sulphate to provide essential oil samples. The essential oil samples were kept in brown vials in the refrigerator at 4° C. until further use. The oil sample was analyzed by GC-MS, and many compounds were identified in the oil, which allowed comparison to the recorded composition of Yarrow essential oil in the literature to further confirm plant identity.

Example 2

Animal Treatment

To study the hepatic protective activity of *Achillea millefolium* essential oil (AEO) on $CdCl_2$-induced hepatic toxicity, male Wistar rats (weighing, 180 g-200 g) were purchased from the Experimental Animal Research Centre, King Saud University, Riyadh, KSA. The animals were randomly divided into four groups (n=8 per group). For Group I (the Control group), the animals were pre-administered with 0.9% NaCl (physiological saline), 2 hours before the injection of 0.9% NaCl (physiological saline) i.p., daily for 7 days. For Group II (the $CdCl_2$ group), the animals were pre-administered with 0.9% NaCl (physiological saline) 2 hours before injection of 6.5 mg/kg $CdCl_2$ i.p. daily for 7 days. For Group III (the AEO group), the animals were pre-administered with 250 mg/kg AEO 2 hours before the injection of 0.9% NaCl (physiological saline) i.p. daily for 7 days. For Group IV (the AEO+$CdCl_2$ group), the animals were pre-administered with 250 mg/kg AEO 2 hours before the injection of 6.5 mg/kg $CdCl_2$ i.p. daily for 7 days. Twenty-four hours after the last treatment, the animals were killed and the liver was quickly removed and weighed.

Example 3

Determination of Cd Concentration

Cd concentration was measured using conventional methods. Liver tissue was weighed and dried in an oven for 4 hours at 250° C. Then, the dried samples were digested with 2 M nitric acid and 2 M hydrochloric acid for 5 hours at 150° C. The samples were diluted with deionized water to 50 ml. Cd concentrations were determined by spectrophotometry at 283.3 nm. The Cd concentrations are expressed as µg/g of wet liver tissue.

Example 4

Biochemical Parameters and Liver Function Test

The activities of alanine transaminase (ALT), aspartate aminotransferase (AST), alkaline phosphatase (ALP), lactate dehydrogenase (LDH) enzymes and γ-glutamyltransferase1 (γGTT1) were determined using ELISA kits.

Example 5

Preparation of Liver Tissue Homogenates

Parts of the frozen liver samples (50 mg) were homogenized in 1 ml ice-cold phosphate buffer saline containing a protease/phosphatase inhibitor cocktail. The homogenates were centrifuged at 10,000×g for 15 minutes at 4° C. and the supernatants were isolated to new tubes. The tubes were kept at −20° C. until further biochemical analysis.

Example 6

Determination of Hepatic Oxidative Stress Markers

Lipid peroxidation was assessed according to the amount of malondialdehyde (MDA). The activities of catalase, superoxide dismutase (SOD) glutathione peroxidase (GSH-Px) and glutathione reductase (GSH-R) were estimated using kits, according to manufacturer protocol.

Example 7

Evaluation of Nuclear Factor Erythroid 2-Related Factor2 (Nrf2) Pathway and NFκB Gene Expression Gene expression for the Nrf2 pathway, including nuclear factor erythroid 2-related factor 2 (Nrf2), hemeoxygenase-1 (HO-1), NAD(P)H: quinone oxidoreductase 1 (NQO1) and Nuclear factor kappa B (NFκB) were quantified via real-time PCR (qPCR) consuming the primers' sequences, shown in Table 1, in agreement with the method described elsewhere. Briefly, RNA was isolated and purified using a Trizol reagent kit (Invitrogen, Carlsbad, CA, USA), then a reverse transcription polymerase chain reaction (RT-PCR) kit (TaKaRa, Kusatsu, Shiga, Japan) following the manufacturer's procedures. qPCR was applied using a SYBR ExScript RT-PCR kit, and quantification examinations were accomplished via an Opticon-2 Real-4 time PCR reactor (MJ Research, Capital Court, Reno, NV, USA). qPCR results were obtained using Step PE Applied Biosystems (Waltham, MA, USA) software. Relative gene expression data were calculated as mentioned earlier by the Livak and Schmittgen method (2-ΔΔCq2) and presented as a fold change. Target gene expressions were assessed and related to the reference gene (β-actin).

TABLE 1

Primer sequences used for qPCR of Nrf2 pathway gene expression.

| TLR pathway | Primer sequence (5' to 3') |
|---|---|
| Nrf2 | 5'-AGGCTGACAAGGCTCGTTATG-3' (sense) (SEQ ID NO: 1)<br>5'-TGTCATCCGCAGCAGTGTTG-3' (antisense) (SEQ ID NO: 2) |
| HO-1 | 5'-CATGACATCCCTTATTCAACCAAG-3' (sense) (SEQ ID NO: 3)<br>5'-GCCATGCCTTGTCTTCAATTG-3' (antisense) (SEQ ID NO: 4) |
| NQO1 | 5'-AGGATGGGAGGTACTCGATC-3' (sense) (SEQ ID NO: 5)<br>5'-AGGCGTCCTTCCTTATATGCTA-3' (antisense) (SEQ ID NO: 6) |
| NFκB | 5'-ATCATCAACATGAGAAACGATCTGTA-3' (sense) (SEQ ID NO: 7)<br>5'-CAGCGGTCCAGAAGACTCAG-3' (antisense) (SEQ ID NO: 8) |
| β-Actin | 5'-TGCTATGTT GCCCTAGACTTCG-3' (sense) (SEQ ID NO: 9)<br>5'-GTTGGCATAGAG GTCTTTACGG-3' (antisense) (SEQ ID NO: 10) |

Example 8

Determination of Liver Inflammatory Markers

Inflammation markers including tumor necrosis factor alpha (TNF-α), interleukin 1β (IL-1β), intracellular adhesion molecule-1 (ICAM-1) and myeloperoxidase (MPO) were measured according to the manufacturer protocol of the Kit.

Example 9

Statistical Analysis

Data were shown as mean±SD. Multiple comparisons were performed using a one-way ANOVA followed by Tukey-Kramer as a post hoc test. The 0.05 level of probability was used as the significance level. Statistical analyses were executed using GraphPad software (version 8, San Diego, CA, USA).

Example 10

Changes in Body Weight and Cd Level in Hepatic Tissue

The final weights of the AEO-treated animals exposed to $CdCl_2$ were significantly greater than $CdCl_2$ alone administered animals (Table 2). $CdCl_2$ injection in rats significantly increased ($p<0.05$) the concentration of Cd in hepatic tissue when related to control group. Whereas, administration of AEO prior to $CdCl_2$-injection decreased the Cd concentration in the hepatic tissue significantly ($p<0.05$) (Table 2).

TABLE 2

Effect of AEO on animals weight, and hepatic Cd concentration in cadmium-administered rats. All values are stated as mean ± SD.

| Parameters | Animal groups | | | |
| --- | --- | --- | --- | --- |
| | Control | AEO | CdCl2 | AEO + CdCl2 |
| Initial weight | 180.37 ± 8.42 | 190.49 ± 7.45 * | 186.31 ± 6.48 | 183.56 ± 7.45 # |
| Final weight | 224.47 ± 7.43 | 220.5 ± 7.490 * | 190.84 ± 4.41 | 214.23 ± 0.12 # |
| Cd concentration (μg/g liver tissue) | 0.024 ± 0.001 | 0.023 ± 0.003 * | 0.74 ± 0.023 | 0.37 ± 0.028 # |

* designates statistically significant compared to control group, and
designates statistically significant compared to CdCl2 group, (p < 0.05) using one-way ANOVA followed by Tukey's post hoc test

Example 11

Changes in Hepatic Function Tests

Figure 1A:
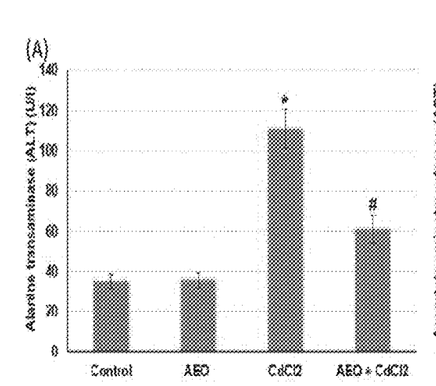
FIGS. 1A-1E are graphs showing effects of *Achillea* Essential Oil (AEO) administration on hepatic function tests including (1A) alanine transaminase (ALT); (1B) aspartate aminotransferase (AST); (1C) alkaline phosphatase (ALP); (1D) lactate dehydrogenase (LDH); and (1E) γ-glutamyl-transferase1 (γGTT1) enzymes in Cd-induced liver toxicity (all values are stated as mean±SD and * designates statistically significant compared to control group, and #designates statistically significant compared to $CdCl_2$ group, (p<0.05) using one-way ANOVA followed by Tukey's post hoc test.
Figure 1B:
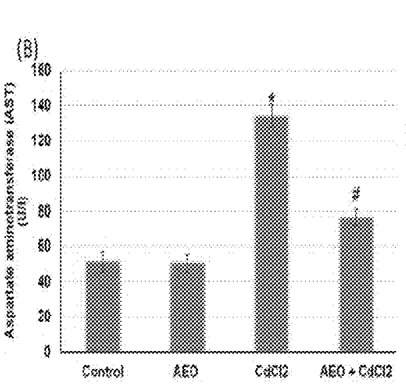
Figure 1C:
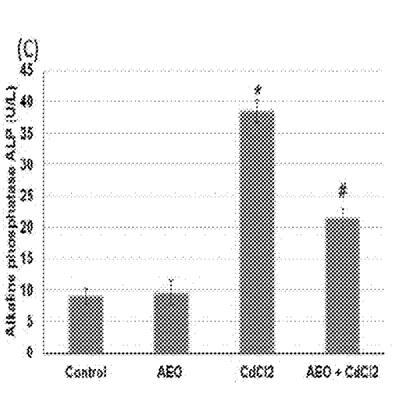
Figure 1D:
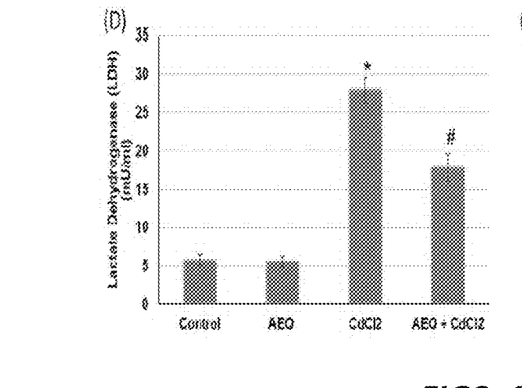
Figure 1E:
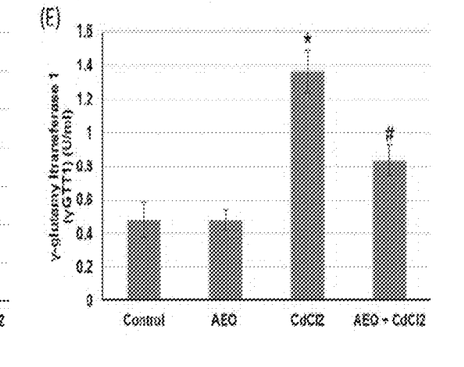

Rats exposed to Cd-induced exhibited liver injury were indicated by the increase in the levels of serum ALT, AST, ALP, LDH and γGTT1 enzymes when compared to control group. Administration of AEO significantly ameliorated these metabolite amplifications (FIGS. 1A-1E).

Example 12

Liver Oxidative Stress

Figure 2A:
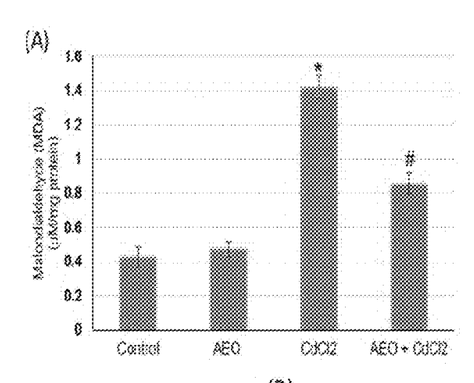
FIGS. 2A-2E are graphs showing effects of *Achillea* Essential Oil (AEO) administration on the hepatic oxidative stress including (2A) MDA; (2B) GSH-Px; (2C) GSH-R; (2D) SOD; and (2E) catalase in Cd-induced liver toxicity (all values are stated as mean±SD. * designates statistically significant compared to control group, and #designates statistically significant compared to $CdCl_2$ group, (p<0.05) using one-way ANOVA followed by Tukey's post hoc test.
Figure 2B:
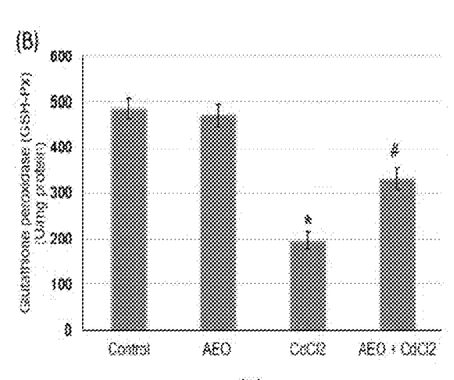
Figure 2C:
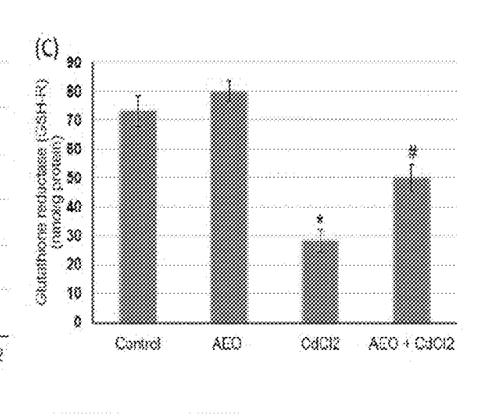
Figure 2D:
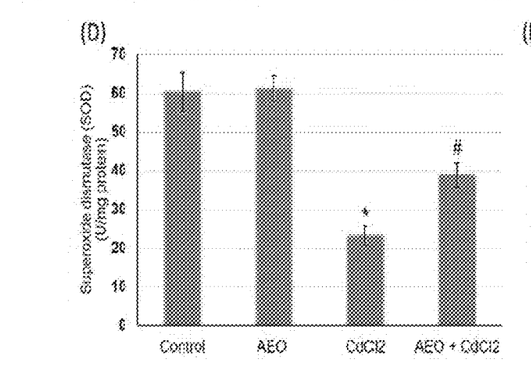
Figure 2E:
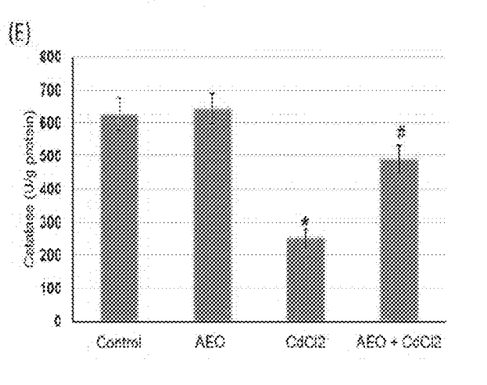

MDA levels were augmented in $CdCl_2$-experienced animals compared to the control, while AEO administration prevented the amplification in MDA level, indicating mitigated lipid peroxidation. Furthermore, in $CdCl_2$ administered rats, the activities of SOD, CAT, GSH-Px and GSH-R were considerably declined, whereas AEO administration enhanced SOD, CAT, GSH-Px and GSH-R activities (FIGS. 2A-2E).

Example 13

Changes on Hepatic Nrf2/HO-1/NQO1 and NFκB Pathway Gene Expression

To counteract oxidative stress, cells have complicated mechanisms of defense against Cd toxicity. One of the most important mechanisms involves the activation of Nrf2 pathway, which leads to the expression of cytoprotective enzymes, such as NAD(P)H: quinone oxidoreductase 1 (NQO1) and heme oxygenase 1 (HO-1). Therefore, to examine the underlying mechanism of AEO on Cd-induced liver toxicity, we explored the mRNA expression levels of Nrf2, HO-1 and NQO1.

In addition, injury caused by Cd triggers numerous inflammatory mediators including NFκB. Therefore, mRNA expression level of NFκB was measured.

Figure 3A:
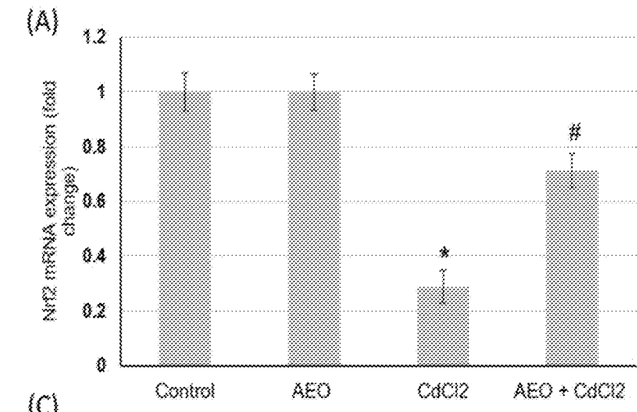
FIGS. 3A-3D are graphs showing effects of *Achillea* Essential Oil (AEO) administration on the gene expression of (3A) nuclear factor erythroid2-related factor2 (Nrf2); (3B) heme oxygenase 1 (HO-1); (3C) NAD(P)H: quinone oxidoreductase 1 (NQO1) and (3D) Nuclear factor kappa B (NFκB) in Cd-induced liver toxicity (all values are stated as mean±SD and * designates statistically significant compared to control group, and #designates statistically significant compared to $CdCl_2$ group, (p<0.05) using one-way ANOVA followed by Tukey's post hoc test.
Figure 3B:
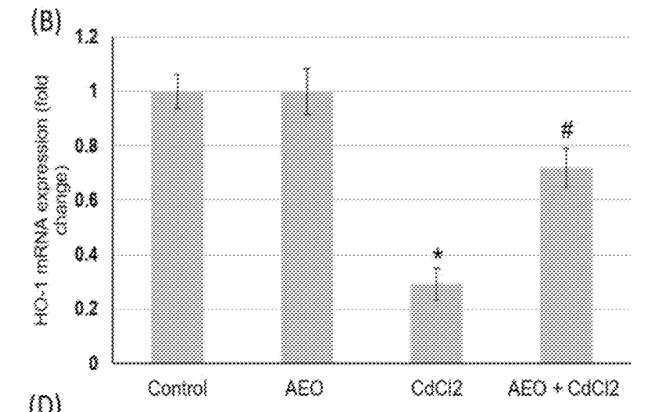
Figure 3C:
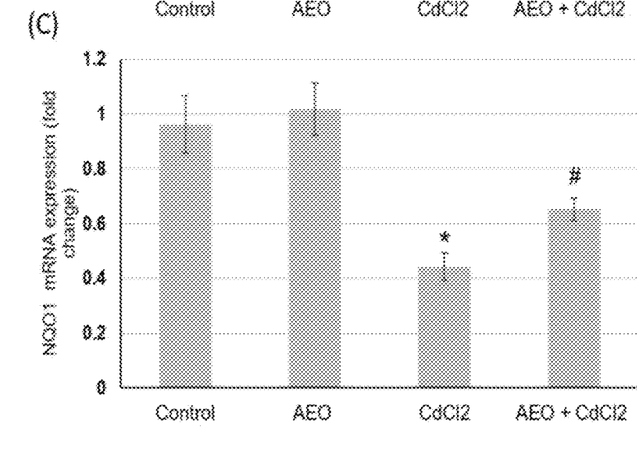
Figure 3D:
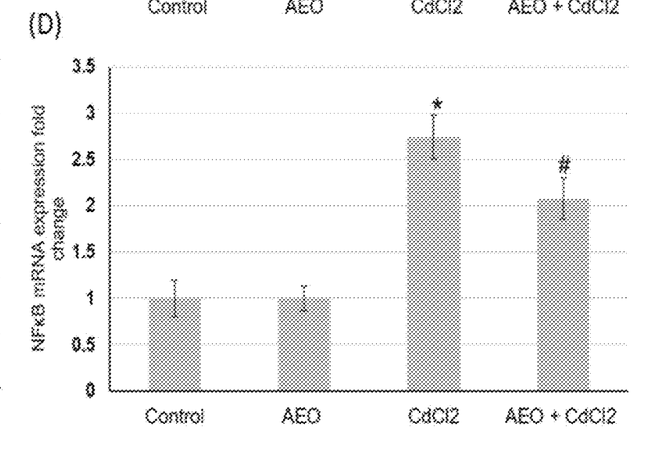

Nrf2, HO-1 and NQO1 mRNA expression levels were decreased in Cd administered rats, whereas AEO increased Nrf2, HO-1 and NQO1 expression, (FIGS. 3A-3E). On the other hand, nuclear NFκB 7 was significantly augmented in the Cd group, whereas NFκB level was substantially diminished in rats receiving AEO with Cd compared to the Cd alone group (FIGS. 3A-3E).

Example 14

Changes in Hepatic Inflammation

Figure 4A:
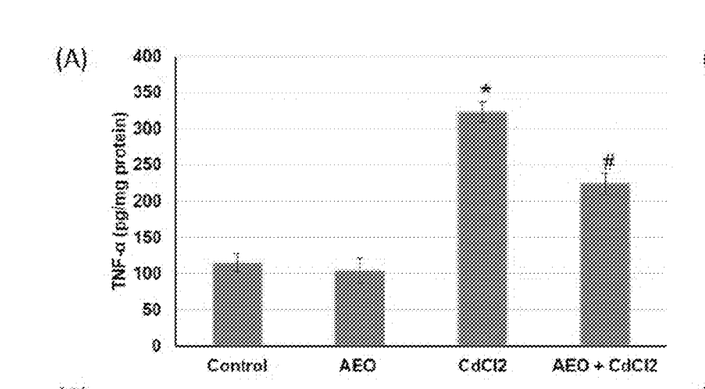
FIGS. 4A-4D are graphs showing effects of *Achillea* Essential Oil (AEO) administration on the hepatic inflammatory mediators including (4A) TNF-α; (4B) IL-1β; (4C) MPO; and (4D) ICAM-1 in Cd-induced liver toxicity (all values are stated as mean±SD and * designates statistically significant compared to control group, and #designates statistically significant compared to $CdCl_2$ group, (p<0.05) using one-way ANOVA followed by Tukey's post hoc test).
Figure 4B:
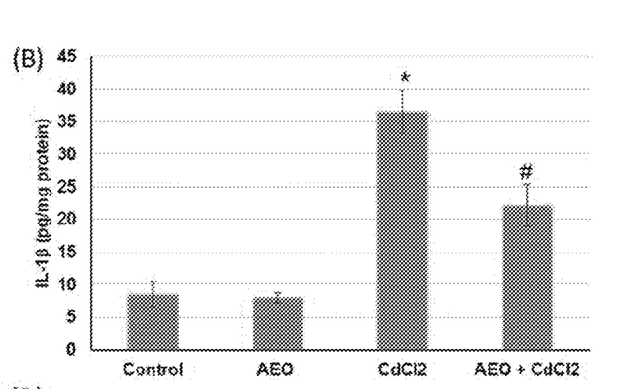
Figure 4C:
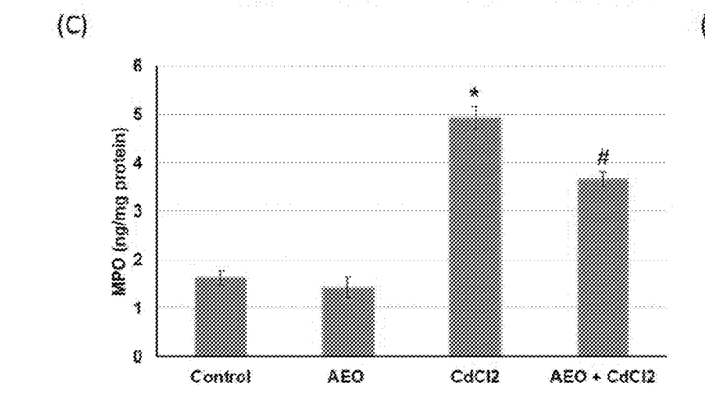
Figure 4D:
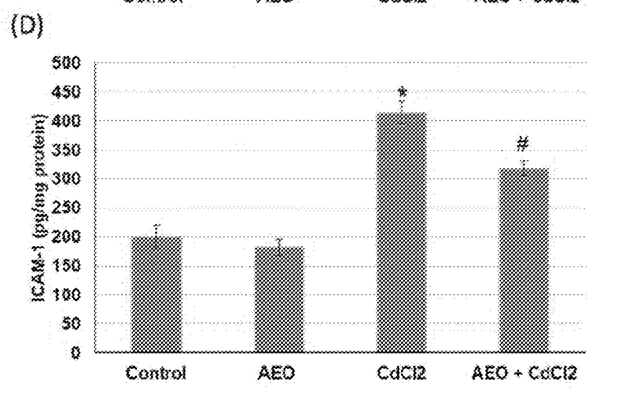

The effect of AEO on inflammation was examined via the detection of several cytokines and inflammatory mediators. TNF-α, IL-1β, MPO and ICAM-1 hepatic levels were augmented in the $CdCl_2$ group, whereas AEO administration distinctly decreased TNF-α, IL-1β, MPO and ICAM-1 hepatic levels (FIGS. 4A-4D).

It is to be understood that the method of preventing a cadmium-induced liver toxicity using a plant product derived from *Achillea millefolium* L. is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of prophylactically protecting against cadmium-induced liver toxicity in a patient exposed to cadmium, comprising:

administering a plant product derived from *Achillea millefolium* L. to a patient in need thereof, wherein the plant product is an essential oil of *Achillea millefolium* L.

2. The method of claim 1, wherein the essential oil of *Achillea millefolium* L. is derived from aerial parts of *Achillea millefolium* L.

3. The method of claim 2, wherein the essential oil of *Achillea millefolium* L. is prepared by a method comprising:

drying the aerial parts of *Achillea millefolium* L. to provide a dried sample;

subjecting the dried sample to hydro-distillation to provide a volatile fraction; and drying the volatile fraction to provide the essential oil.

4. The method of claim 1, wherein the administration of the essential oil of *Achillea millefolium* L. increases Nrf2 expression in the patient.

5. The method of claim 1, wherein the administration of the essential oil of *Achillea millefolium* L. increases HO-1 expression in the patient.

6. The method of claim 1, wherein the administration of the essential oil of *Achillea millefolium* L. increases NQO1 expression in the patient.

7. The method of claim 1, wherein the administration of the essential oil of *Achillea millefolium* L. decreases NFκB levels in the patient.

8. A method of prophylactically protecting against cadmium-induced liver toxicity in a patient exposed to cadmium, comprising:
   administering a pharmaceutical composition comprising a plant product derived from *Achillea millefolium* L. and a pharmaceutically acceptable carrier to a patient in need thereof, wherein the plant product is an essential oil of *Achillea millefolium* L.

9. The method of claim 8, wherein the essential oil of *Achillea millefolium* L. is prepared by a method comprising:
   drying the aerial parts of *Achillea millefolium* L. to provide a dried sample;
   subjecting the dried sample to hydro-distillation to provide a volatile fraction; and
   drying the volatile fraction to provide the essential oil.

10. The method of claim 8, wherein the administration of the essential oil of *Achillea millefolium* L. increases Nrf2 expression in the patient.

11. The method of claim 8, wherein the administration of the essential oil of *Achillea millefolium* L. increases HO-1 expression in the patient.

12. The method of claim 8, wherein the administration of the essential oil of *Achillea millefolium* L. increases NQO1 expression in the patient.

13. The method of claim 8, wherein the administration of the essential oil of *Achillea millefolium* L. decreases NFκB levels in the patient.

14. A method of prophylactically protecting against cadmium-induced liver toxicity in a patient exposed to cadmium, comprising:
   administering an essential oil of *Achillea millefolium* L to a patient in need thereof.

15. The method of claim 14, wherein the essential oil of *Achillea millefolium* L. is prepared by a method comprising:
   drying the aerial parts of *Achillea millefolium* L. to provide a dried sample;
   subjecting the dried sample to hydro-distillation to provide a volatile fraction; and
   drying the volatile fraction to provide the essential oil.

16. The method of claim 14, wherein the administration of the essential oil of *Achillea millefolium* L. increases Nrf2 expression in the patient.

17. The method of claim 14, wherein the administration of the essential oil of *Achillea millefolium* L. increases HO-1 expression in the patient.

18. The method of claim 14, wherein the administration of the essential oil of *Achillea millefolium* L. increases NQO1 expression in the patient.

19. The method of claim 14, wherein the administration of the essential oil of *Achillea millefolium* L. decreases NFκB levels in the patient.

* * * * *

SEQUENCE LISTING

```
Sequence total quantity: 10
SEQ ID NO: 1            moltype = DNA   length = 21
FEATURE                 Location/Qualifiers
source                  1..21
                        mol_type = other DNA
                        organism = synthetic construct
SEQUENCE: 1
aggctgacaa ggctcgttat g                                                21

SEQ ID NO: 2            moltype = DNA   length = 20
FEATURE                 Location/Qualifiers
source                  1..20
                        mol_type = other DNA
                        organism = synthetic construct
SEQUENCE: 2
tgtcatccgc agcagtgttg                                                  20

SEQ ID NO: 3            moltype = DNA   length = 24
```

```
                           -continued

FEATURE             Location/Qualifiers
source              1..24
                    mol_type = other DNA
                    organism = synthetic construct
SEQUENCE: 3
catgacatcc cttattcaac caag                                      24

SEQ ID NO: 4        moltype = DNA  length = 21
FEATURE             Location/Qualifiers
source              1..21
                    mol_type = other DNA
                    organism = synthetic construct
SEQUENCE: 4
gccatgcctt gtcttcaatt g                                         21

SEQ ID NO: 5        moltype = DNA  length = 20
FEATURE             Location/Qualifiers
source              1..20
                    mol_type = other DNA
                    organism = synthetic construct
SEQUENCE: 5
aggatgggag gtactcgatc                                           20

SEQ ID NO: 6        moltype = DNA  length = 22
FEATURE             Location/Qualifiers
source              1..22
                    mol_type = other DNA
                    organism = synthetic construct
SEQUENCE: 6
aggcgtcctt ccttatatgc ta                                        22

SEQ ID NO: 7        moltype = DNA  length = 26
FEATURE             Location/Qualifiers
source              1..26
                    mol_type = other DNA
                    organism = synthetic construct
SEQUENCE: 7
atcatcaaca tgagaaacga tctgta                                    26

SEQ ID NO: 8        moltype = DNA  length = 20
FEATURE             Location/Qualifiers
source              1..20
                    mol_type = other DNA
                    organism = synthetic construct
SEQUENCE: 8
cagcggtcca gaagactcag                                           20

SEQ ID NO: 9        moltype = DNA  length = 22
FEATURE             Location/Qualifiers
source              1..22
                    mol_type = other DNA
                    organism = synthetic construct
SEQUENCE: 9
tgctatgttg ccctagactt cg                                        22

SEQ ID NO: 10       moltype = DNA  length = 22
FEATURE             Location/Qualifiers
source              1..22
                    mol_type = other DNA
                    organism = synthetic construct
SEQUENCE: 10
gttggcatag aggtctttac gg                                        22
```